(12) United States Patent
Wershofen et al.

(10) Patent No.: US 7,368,595 B2
(45) Date of Patent: May 6, 2008

(54) PROCESS FOR THE PRODUCTION OF LIGHT-COLORED ISOCYANATES

(75) Inventors: Stefan Wershofen, Mönchengladbach (DE); Torsten Hagen, Essen (DE); Christian Steffens, Köln (DE); Jeffrey Bolton, Düsseldorf (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 11/651,720

(22) Filed: Jan. 10, 2007

(65) Prior Publication Data

US 2007/0167646 A1    Jul. 19, 2007

(30) Foreign Application Priority Data

Jan. 17, 2006    (DE) .................... 10 2006 002 157

(51) Int. Cl.
*C07C 263/00*    (2006.01)
(52) U.S. Cl. .................. 560/347; 560/336; 560/338
(58) Field of Classification Search .............. 560/347, 560/336, 338
See application file for complete search history.

(56) References Cited

U.S. PATENT DOCUMENTS

| | | | |
|---|---|---|---|
| 4,465,639 A | 8/1984 | Hatfield, Jr. .......... 260/453 PH |
| 4,774,357 A | 9/1988 | Keggenhoff et al. ........ 560/352 |
| 5,207,942 A | 5/1993 | Scherzer et al. ......... 252/182.2 |
| 5,208,368 A | 5/1993 | Scherzer et al. ........... 560/333 |
| 5,312,971 A | 5/1994 | Adkins et al. .............. 560/347 |
| 5,364,958 A | 11/1994 | Ishida et al. ................. 560/359 |
| 5,386,059 A | 1/1995 | Bolton et al. ............... 564/331 |
| 5,484,819 A | 1/1996 | Bolton et al. ............... 521/155 |
| 6,140,382 A | 10/2000 | Gallus et al. ............... 521/155 |
| 6,576,788 B1 | 6/2003 | Penzel et al. ............... 560/333 |
| 6,900,348 B1 * | 5/2005 | Reif et al. ................... 560/347 |
| 6,942,842 B2 | 9/2005 | Breuer et al. .......... 423/244.01 |
| 2004/0141901 A1 | 7/2004 | Breuer et al. .......... 423/244.09 |
| 2005/0025693 A1 | 2/2005 | Bagals et al. ............... 423/416 |

FOREIGN PATENT DOCUMENTS

| | | |
|---|---|---|
| CA | 2038126 | 9/1991 |
| EP | 0 538 500 B1 | 2/1995 |

OTHER PUBLICATIONS

Database Caplus [Online] Chemical Abstracts Service, Columbus, Ohio, US; Manabe, Akiyoshi et al: "Polycarbonates with excellent color tone and durability and their manufacture" XP002435080 Database accession No. 2000:580011 & JP 2000 230046 A (Teijin Chemicals Ltd., Japan) Aug. 22, 2000.

* cited by examiner

*Primary Examiner*—Shaojia Anna Jiang
*Assistant Examiner*—Sudhakar Katakam
(74) *Attorney, Agent, or Firm*—Lyndanne M. Whalen; John E. Mrozinski, Jr.

(57) ABSTRACT

The invention relates to an improved process for the production of isocyanates by the reaction of an amine or a mixture of two or more amines with phosgene, the improvement involving the phosgene containing less than about 100 ppm of sulfur in elemental or bound form. The inventive process yields light-colored isocyanates that are suitable for the production of polyurethanes or their precursors (e.g. prepolymers) without the treatment processes heretofore required.

7 Claims, No Drawings

PROCESS FOR THE PRODUCTION OF LIGHT-COLORED ISOCYANATES

FIELD OF THE INVENTION

The invention relates to a process for the production of light-colored isocyanates by the reaction of an amine or a mixture of two or more amines with phosgene, wherein the phosgene used contains less than 100 ppm of sulfur in elemental or bound form.

BACKGROUND OF THE INVENTION

Isocyanates and isocyanate mixtures are produced according to the prior art by phosgenation of the corresponding amines. For polyurethane foams, for example, di- or polyfunctional aromatic isocyanates of the diphenylmethane series (MDI) are employed. As a result of the production process, after phosgenation and subsequent work-up (removal of the solvent; removal of monomeric MDI) dark-colored products are often obtained, which in turn give polyurethane foams with a yellowish discoloration or other polyurethane (PUR) materials that are also discolored. This is undesirable, because this coloring adversely affects the overall visual impression and allows slight inhomogeneities to become evident, e.g. as streaks in the foams obtained. Light-colored isocyanates, or isocyanates that contain a reduced quantity of coloring components, are therefore preferred as raw materials.

There has therefore been no lack of attempts to obtain isocyanates, and particularly the di- and polyisocyanates of the diphenylmethane series (MDI), with a light color. Numerous methods for the empirical color lightening of MDI are known. However, the nature of the problematic coloring substances has hitherto been clarified only inadequately.

The previously known processes can be divided into four groups:

1. Processes in which the di- and polyamines of the diphenylmethane series (MDA) used as starting material have been subjected to a treatment and/or purification:

EP-A 0 546 398 describes a process for the production of MDI in which the MDA used as starting material is acidified prior to phosgenation.

EP-A 0 446 781 relates to a process for the production of MDI in which the MDA is first treated with hydrogen and subsequently subjected to a phosgenation, a relatively light-colored MDI being obtained.

The above-mentioned processes give only a slight improvement in the color, as the coloring substances in the MDI have been found on the basis of experience not only to consist of certain by-products from MDA production but also to result from color precursors which are formed by side-reactions during the phosgenation.

2. Process engineering solutions in the phosgenation process:

U.S. Pat. No. 5,364,958 relates to a process for the production of isocyanates in which, after the phosgenation, the phosgene is removed completely at low temperature and the isocyanate is subsequently treated with HCl gas at elevated temperatures.

DE-A-1981 7691 describes a process for the production of MDI having a reduced content of chlorinated by-products and a reduced iodine color value by adherence to defined parameters in the phosgenation reaction. In particular, adherence to particular phosgene/HCl ratios in the reaction step is required. This process has the disadvantage that a variation of the parameters in the phosgenation is made difficult and the quality of the phosgenation is very sensitive as a result. In addition, the lack of flexibility in the parameters in the phosgenation makes the phosgenation very difficult to carry out in practice and requires a high engineering effort.

Another way of improving the color of isocyanates is, according to EP-B 1 187 808, the use of phosgene with low bromine and/or iodine contents.

Although processes of the type mentioned attempt to remove the components causing the discoloration at the correct point, they are not efficient enough, both because of their high technical requirements and also in terms of their color-lightening effect, given that only slight degradation of color precursors occurs owing to incomplete chemical reactions.

3. Addition of color-lightening additives to the crude isocyanate product after the phosgenation and before the work-up, e.g. by distillation:

EP-A 0 581 100 relates to a process for the production of isocyanates in which a chemical reducing agent is added after the phosgenation and before the removal of solvent, which according to this document also gives light-colored products.

According to U.S. Pat. No. 4,465,639, water is added to the crude product obtained after the phosgenation in order to lighten its color. EP-A 538 500, EP-A 0 445 602 and EP-A 0 467 125 describe the addition of carboxylic acids, alkanols or polyether polyols after the phosgenation for the same purpose.

Although the methods of lightening the color described above are efficient, they have disadvantages in that the additives not only lighten the color but also undergo reactions with the isocyanates obtained as product, generally resulting, for example, in an undesirable reduction in the isocyanate content. In addition, there is the risk of formation of undesirable by-products in the MDI.

4. After-treatment of the end product:

EP-A 0 133 538 describes the purification of isocyanates by extraction, giving fractions of a light-colored MDI.

EP-A 0 561 225 relates to a process for the production of isocyanates or isocyanate mixtures which, according to this document, contain no coloring components, wherein the isocyanates are subjected to a hydrogen treatment at a pressure of 1 to 150 bar and a temperature of 100 to 180° C. after the phosgenation of the corresponding amines. According to the examples described there, isocyanate end products are hydrogenated as such or in the form of their solutions in suitable solvents.

These color-improving after-treatments of the isocyanate end products after complete removal of the solvent at elevated temperature are likewise not very efficient, because the high temperatures occurring during the work-up, in particular during the distillation of the solvent and optionally of monomeric MDI (diisocyanates), have already resulted in the formation of stable coloring substances which can be chemically degraded only with difficulty.

SUMMARY OF THE INVENTION

The present invention provides a simple and economical process for the production of light-colored isocyanates containing no coloring components or only small quantities thereof. The inventive process should not require the above-mentioned treatment steps and yet should lead to light-colored isocyanates that are suitable for the production of polyurethanes or their precursors (e.g. prepolymers).

Surprisingly, it was possible to produce such light-colored isocyanates according to the invention by using phosgene containing less than about 100 ppm, preferably less than about 60 ppm, more preferably less than about 20 ppm of sulfur in elemental or bound form in the production of the isocyanates. The range statement "less than about 100 ppm of sulfur" means that less than about 100 ppm of sulfur, based on the weight of phosgene used, is contained in the phosgene used.

DETAILED DESCRIPTION OF THE INVENTION

The present invention will now be described for purposes of illustration and not limitation. Except in the operating examples, or where otherwise indicated, all numbers expressing quantities, percentages, and so forth in the specification are to be understood as being modified in all instances by the term "about."

The present invention provides an improved process for the production of isocyanates by the reaction of an amine or a mixture of two or more amines with phosgene, the improvement involving the phosgene containing less than 100 ppm, preferably less than 60 ppm, more preferably less than 20 ppm of sulfur in elemental or bound form.

Sulfur in elemental form is sulfur which is present in the form of molecules exclusively containing sulfur. Sulfur in bound form is to be understood as compounds or molecules which, in addition to sulfur, also contain other atoms different from sulfur, such as for example hydrogen sulfide.

The phosgene used within the framework of the present invention contains less than 100 ppm, preferably less than 60 ppm, more preferably less than 20 ppm of sulfur in the form of elemental sulfur or in the form of sulfur-containing compounds.

The process according to the invention leads to isocyanates which can be used without any additional process steps for the production of urethane compounds such as polyurethanes or their precursors (e.g. prepolymers) and which display no or only slight coloration.

Surprisingly, the process according to the invention leads to light-colored isocyanates, as it was hitherto unknown that even extremely small traces of elemental or bound sulfur in the phosgene are sufficient to have an undesirable effect on the product color of the isocyanates produced therewith.

The phosgene used for the production of isocyanates preferably has a certain content of elemental or bound sulfur. The sulfur content in the phosgene substantially results from the carbon monoxide (CO) used to produce the phosgene, which contains a certain proportion of sulfur depending on its origin. The sulfur content again results predominantly from the sulfur content of the raw materials used to produce the CO.

The phosgene with a low sulfur content used in the process according to the invention can be produced by various methods known to the person skilled in the art. One way of guaranteeing a low sulfur content in phosgene is, for example, the use of starting compounds in phosgene production that already have a correspondingly low sulfur content. In particular, the use of CO with a correspondingly low sulfur content is suitable here. Processes for the production of CO with a low sulfur content are known to those skilled in the art.

Thus, for example, it is possible to use CO obtained by coal gasification, steam reforming, $CO_2$ reforming, partial oxidation of hydrocarbons or other processes. CO can also be obtained by separation from gas mixtures containing CO. Processes of this type for the production or obtaining of CO are described e.g. in *Chemische Technik* (editors: Dittmeyer, Keim, Kreysa, Oberholz), $5^{th}$ edition, Vol. 4, pages 981-1007.

In principle, it is possible to use any CO meeting the above specification, i.e. containing less than 100 ppm, preferably less than 60 ppm, more preferably less than 20 ppm of sulfur, within the framework of the present invention.

The low sulfur content required in the CO is achieved in that raw materials that are virtually sulfur-free or have a sufficiently low sulfur content are used to produce or obtain the CO. It is unimportant how the freedom from sulfur or the sufficiently low sulfur content of the raw materials used to produce or obtain the CO is achieved.

Another way of achieving the low sulfur content required in the CO lies in removing sulfur present in elemental or bound form from the CO to be used. Numerous processes that serve this purpose are described in the literature. The removal of sulfur-containing impurities, such as e.g. $H_2S$, according to US-A1-2005/0025693 by bringing into contact the CO-containing gas stream with activated carbon impregnated with a metal oxide can be mentioned as an example. Another possibility is the conversion of inorganic and organic sulfur compounds in the presence of water vapor on an aluminum oxide contact at elevated temperature and passing of the gas mixture obtained over a material containing iron hydroxide in the presence of water vapor and defined quantities of oxygen according to DE-A1-103 01 434, for example. DE-A1-103 01 434 also cites other ways of freeing CO from sulfur-containing impurities.

The largely sulfur-free CO obtainable in this way can then be converted to phosgene within the framework of conventional and known processes as described e.g. in *Ullmanns Enzyklopädie der industriellen Chemie*, $3^{rd}$ edition, vol. 13, pages 494-500.

Another way of obtaining phosgene with a low content of elemental or bound sulfur is the removal of elemental or bound sulfur from the phosgene itself. Here again, all common separation processes, e.g. distillation, adsorption etc., can be used in principle. Ultimately, adherence to the above-mentioned upper limit for the concentration of elemental or bound sulfur is required for the process according to the invention.

The isocyanate production taking place by the process according to the invention is carried out by reacting an amine or a mixture of two or more amines with phosgene, preferably with an excess of phosgene. In principle, it is possible to employ all processes known to the person skilled in the art in which a primary amine or a mixture of two or more primary amines is reacted with phosgene to form one or more isocyanate groups.

In a preferred embodiment of the process according to the invention, the reaction of the amine or of the mixture of two or more amines with the phosgene is carried out in a solvent or a mixture of two or more solvents.

All solvents suitable for the production of isocyanates can be used as the solvent. These are preferably inert, aromatic, aliphatic or alicyclic hydrocarbons or their halogenated derivatives. Examples of these solvents are aromatic compounds, such as mono- or dichlorobenzene, e.g. o-dichlorobenzene, toluene, xylenes, naphthalene derivatives such as tetralin or decalin, alkanes with about 5 to about 12 carbon atoms, such as hexane, heptane, octane, nonane or decane, cycloalkanes such as cyclohexane, inert esters and inert ethers such as ethyl or butyl acetate, tetrahydrofuran, dioxane or diphenyl ether.

Suitable amines are, in principle, all primary amines capable of a suitable reaction with phosgene to form isocyanates. In principle, all linear or branched, saturated or unsaturated, aliphatic or cycloaliphatic or aromatic primary mono-, di- or polyamines are suitable, provided they can be reacted with phosgene to form isocyanates. Examples of suitable amines are 1,3-propylendiamine, 1,4-butylenediamine, 1,5-pentamethylenediamine, 1,6-hexamethylene and the corresponding higher homologues of this series, isophoronediamine (IPDA), diaminodicyclohexylmethane, cyclohexyldiamine, cyclohexylamine, aniline, phenylenediamine, p-toluidine, naphthalenediamine and particularly 1,5-naphthylenediamine, toluenediamine and particularly 2,4- or 2,6-toluenediamine or mixtures thereof, di- and polyamines of the diphenylmethane series and particularly 4,4'-, 2,4'- or 2,2'-diphenylmethanediamine or mixtures thereof and also higher molecular weight isomeric, oligomeric or polymeric derivatives of the above-mentioned amines and polyamines. In a preferred embodiment of the present invention, the amine used is an amine of the diphenylmethane series or a mixture of di- and/or polyamines of the diphenylmethane series.

After going through the process according to the invention, the above-mentioned compounds are in the form of the corresponding isocyanates, e.g. as hexa-methylene 1,6-diisocyanate, isophorone diisocyanate, diisocyanatodicyclohexylmethane, cyclohexyl isocyanate, cyclohexyl diisocyanate, phenyl isocyanate, phenylene diisocyanate, 4-tolyl isocyanate, naphthalene diisocyanate and particularly naphthalene 1,5-diisocyanate, toluene diisocyanate and particularly toluene 2,4- or 2,6-diisocyanate or corresponding mixtures thereof, di- and polyisocyanates of the diphenylmethane series and particularly diphenylmethane 4,4'-, 2,4'- or 2,2'-diisocyanate or mixtures of two or more thereof, and as higher molecular weight oligomeric or polymeric derivatives of the above-mentioned isocyanates or as mixtures of two or more of the above-mentioned isocyanates or isocyanate mixtures.

In a preferred embodiment of the present invention, the amines used are the isomeric, primary diphenylmethanediamines (MDA) or their oligomeric or polymeric derivatives, i.e. the di- and polyamines of the diphenylmethane series. Diphenylmethanediamine, its oligomers or polymers are obtained, for example, by condensation of aniline with formaldehyde. Such oligoamines or polyamines or mixtures thereof are also used in a preferred embodiment of the invention.

The reaction of the low-sulfur or even sulfur-free phosgene with one of the above-mentioned amines or a mixture of two or more of these amines in the process according to the invention can take place continuously or batchwise in one or more steps. If a single-step reaction is carried out, this reaction preferably takes place at 60 to 200° C., more preferably at 130 to 180° C.

In another embodiment of the invention, the reaction can, for example, be carried out in two steps. Here, in a first step, the reaction of the phosgene with the amine or the mixture of two or more amines is preferably carried out at a temperature of between 0 and 130° C., more preferably 20 to 110° C., most preferably 40 to 70° C., with a time of 1 minute to 2 hours preferably being allowed for the reaction between amine and phosgene. Subsequently, in a second step, the temperature is increased preferably to 60 to 190° C., more preferably 70 to 170° C., over a period of preferably 1 minute to 5 hours, particularly preferably 1 minute to 3 hours.

In one embodiment of the invention, the reaction is carried out in two steps.

During the reaction, an elevated absolute pressure can preferably be applied, which is 100 bar or less, preferably 1 bar to 50 bar, more preferably 2 bar to 25 bar, most preferably 3 bar to 12 bar. However, the reaction can also be carried out without excess pressure.

In another embodiment of the invention, the reaction is carried out at ambient pressure, i.e. generally about 1 bar absolute. In a further embodiment, the reaction can also be carried out at a pressure below ambient pressure.

Excess phosgene is preferably removed at a preferred temperature of 50 to 200° C. after the reaction. The removal of remaining traces of solvent is preferably carried out under reduced pressure. The absolute pressure is preferably 500 mbar or less, more preferably less than 100 mbar. In general, the various components are separated off in the order of their boiling points; it is also possible to separate off mixtures of the various components in a single process step.

EXAMPLES

The present invention is further illustrated, but is not to be limited, by the following examples.

General preparation specification:

Starting materials:

MDA, obtained by acid-catalyzed condensation of aniline with formaldehyde, substantially consisting of 4,4'-MDA, 2,4'-MDA, 2,2'-MDA (2-ring MDA) and higher homologues and isomers; content of 2-ring MDA 61.0 wt.% chlorobenzene anhydrous phosgene 50 g of MDA were dissolved in 255 ml of chlorobenzene, heated to 55° C. and added to a solution of 105 g of phosgene in 310 ml of chlorobenzene temperature-controlled at 0° C., with intensive stirring. The sulfur content of the phosgene used can be taken from the table below. The suspension was heated to 100° C. within 45 minutes while passing through phosgene, and heated at reflux temperature for 10 minutes. After a further 10 minutes at this temperature, the solvent was distilled off under reduced pressure to a sump temperature of 100° C. The crude isocyanate was heated in a distillation apparatus using a hot air blower under a pressure of 4 to 6 mbar until the first product transition occurred and cooled to room temperature within 5 to 10 minutes. 1.0 g of the isocyanate thus obtained was dissolved in chlorobenzene and diluted to 50 ml with chlorobenzene. The extinction of the solution thus obtained was determined at the two wavelengths, 430 nm and 520 nm. A Dr. Lange LICO 300 photometer was used as the measuring instrument. The results are summarized in the following table.

A comparison of Examples 1 to 4 with the Comparative Examples 1 and 2 shows that the use of low-sulfur phosgene led to isocyanates with low color values.

|  | S (ppm) | E at 430 nm | E at 520 nm |
| --- | --- | --- | --- |
| Example 1 | 0 | 0.100 | 0.008 |
| Example 2 | 20 | 0.105 | 0.016 |
| Example 3 | 60 | 0.116 | 0.024 |
| Example 4 | 80 | 0.130 | 0.030 |
| Comparative Example 1 | 250 | 0.162 | 0.060 |
| Comparative Example 2 | 500 | 0.241 | 0.121 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In an improved process for the production of isocyanates by the reaction of an amine or a mixture of two or more amines with phosgene, the improvement comprising including phosgene containing less than 100 ppm of sulfur in elemental or bound form.

2. The process according to claim 1, wherein the phosgene contains less than about 60 ppm of sulfur in elemental or bound form.

3. The process according to claim 1, wherein the phosgene contains less than about 20 ppm of sulfur in elemental or bound form.

4. The process according to claim 1, wherein the reaction is carried out in a solvent.

5. The process according to claim 1, wherein the amine is a di- and polyamines of the diphenylmethane series.

6. The process according to claim 1, wherein the amine is toluene diaamine.

7. The process according to claim 1, wherein the amine is hexamethylenediamine or isophoronediamine.

* * * * *